United States Patent [19] [11] 4,360,673
Berger et al. [45] Nov. 23, 1982

[54] 5-PHENYL-1,3-ALKANO-1,2,3,4,4A,9B-HEXAHYDROPYRIDO [4,3-B]INDOLES

[75] Inventors: Joel G. Berger, Verona; Pirouz Tahbaz, Cedar Grove, both of N.J.

[73] Assignee: Schering Corporation, Kenilworth, N.J.

[21] Appl. No.: 136,016

[22] Filed: Mar. 31, 1980

[51] Int. Cl.³ .................. C07D 471/18; A61K 31/40
[52] U.S. Cl. ........................................ 546/70; 424/256
[58] Field of Search ..................... 546/70; 260/326.31

[56] References Cited

U.S. PATENT DOCUMENTS 3,925,409 12/1975 Welch et al. .................. 260/326.31

Primary Examiner—Donald G. Daus
Assistant Examiner—D. B. Springer
Attorney, Agent, or Firm—Gerald S. Rosen; Carver C. Joyner; Bruce M. Eisen

[57] ABSTRACT

This invention relates to 5-phenyl-1,3-alkano-1,2,3,4,4a,9b-hexahydropyrido [4,3-b]indoles which are antidepressants useful in the treatment of mental depression.

6 Claims, No Drawings

5-PHENYL-1,3-ALKANO-1,2,3,4,4a,9b-HEXAHYDROPYRIDO [4,3-b]INDOLES

This invention relates to certain substituted hexahydropyrido [4,3-b]indoles, the pharmaceutical compositions and formulations thereof, to the novel processes and intermediates therefor, and to their use as antidepressant agents suitable for the treatment of mental depression of either an endogenous or reactive mixture.

In one of its composition of matter aspects, this invention relates to 5-phenyl-1,3-alkano-1,2,3,4,4a,9b-hexahydropyrido [4,3-b]indoles of the formula

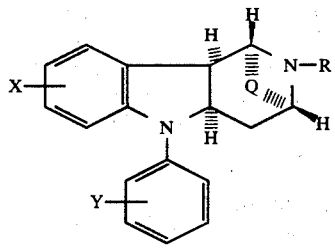

and to their pharmaceutically acceptable quaternary and acid addition salts wherein R is hydrogen or lower alkyl, X and Y each are hydrogen, hydroxy, lower alkoxy or lower alkyl, Q is $(CH_2)_n$ wherein n is two or three.

As used herein, the term "lower" as it modifies such radicals as alkoxy or alkyl and the like, embraces those straight and branched radicals having one to six carbon atoms including such preferred radicals as methyl, ethyl, methoxy and ethoxy although such other radicals as propyl, t-butyl, n-butyl, pentyl and hexyl (and the corresponding alkoxyl manifestations thereof) are contemplated. The "alkano" bridge between the 1- and 3-positions of the pyrido moiety may either be ethano or propano, with ethano being preferred. In those instances wherein X is other than hydrogen it is preferred that the substituent be located in either the 7- or 8-position of the heterocyclic nucleus, preferably the 8-position, although the 6- and 9-positions are also contemplated. Similarly, the 5-phenyl moiety may be substituted with a "Y" substituent in any of the ortho, meta or para positions, although it is preferred that said substituents be located in the para-position.

The acid addition salts preferably include the mineral acid salts such as those prepared from acids as hydrochloric acid, phosphoric acid, sulfuric acid, although such other acid addition salts as those produced from maleic acid, citric acid and other well-known pharmaceutically acid addition forming acids are contemplated. The quaternary salts preferably include those prepared from such organic halides as methyl iodide, ethyl iodide, benzyl chloride and the like, although all of the usual quaternary salts are contemplated.

It is also obvious to one skilled in the art that the compounds of this invention (I) may be produced as racemic mixtures of their dextro- and levorotary-isomers whose separation may be effected by the usual and well known techniques such as by the fractional crystallization of salts of optically active acids, or by preparing a designated intermediate which intermediate, when chemically processed to the final product will produce the desired optical active product directly. Thus, throughout the specification and claims, the d-, and l- and the racemic d,l-mixtures of the compounds of formula I are fully contemplated as part of this invention.

The tangible embodiments of this invention, in the form of their free base or quaternary or acid addition salts thereof, possess the inherent applied use characteristics of exerting a central nervous system effect in that they exert an anti-depressant effect and therefore as such are therapeutically useful.

In general, the compounds of this invention are prepared by standard and well-known techniques from the appropriate starting materials. Preferably an appropriately X,Y-substituted diaryl hydrazine (II) (in the form of an acid salt, e.g., a diaryl hydrazine hydrochloride) is condensed with the appropriate N-protected, 2,6-alkylene-4-piperidone (III) to produce a diaryl hydrazone intermediate (IV). The intermediate is isolated, the N-protective group (R' if used) is removed and the resulting hydrazone (V) is cyclized by the Fischer indole synthesis to the 1,2,3,4-tetrahydro-1,3-alkano-5-phenyl-pyrido [4,3-b]-indole (VI). This intermediate (VI) is chemically reduced to the desired 1,2,3,4,4a,9b-1,3 alkano-5 phenylpyrido [4,3-b] indole (I). Alternatively, the protected diaryl hydrazone (IV) may be directly cyclized via the Fischer indole procedure to give a protected indole, from which the protecting group may be subsequently removed. Obviously, in those instances wherein it is desired to produce compounds having an alkyl substituent at the 2-position of the indole, then compound (I) wherein X and Y are hydrogen is N-alkylated by standard procedures. Similarly, in those instances wherein it is desired to produce compounds having a halogeno radical as X and/or Y, then compound (I) wherein X and Y are hydrogen is treated with elemental halogen according to standard halogenating techniques.

Reaction Scheme

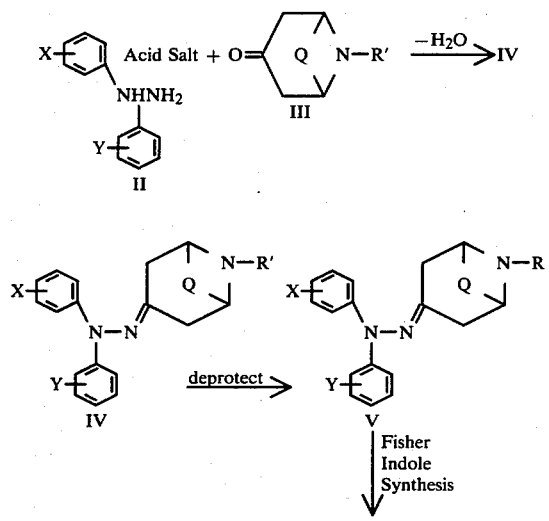

-continued
Reaction Scheme

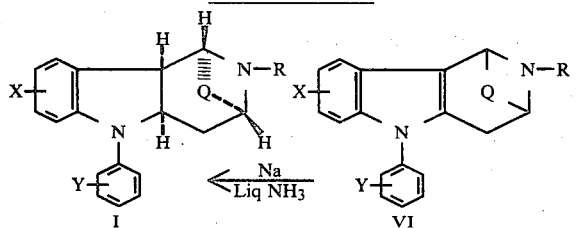

wherein R' is a removable protecting group (e.g.,

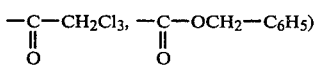

X,Y and Q are as previously defined and R is hydrogen.

As stated above, the chemical transformations required to prepare the compounds of this invention are well known standard reactions. For example, the initial condensation of the diaryl hydrazine (II) and the 2,6-aklylene-4-piperidone (III) (i.e., a tropinone or a granitanone) is effected by heating the reactants together whilst in pyridine as the solvent. Of course in those instances wherein the final product (I) contains a lower alkyl radical at the 2-position then the protecting group need not be present but rather, the 2,6-alkylene-4-piperidone (III) will possess a lower alkyl radical on its nitrogen atom. The deprotection of the N-protecting group (e.g., —CO$_2$CH$_2$CCl$_3$) is effected by chemical reduction of the diaryl hydrazone (IV) utilizing zinc in acetic acid at temperatures of about 40° C. to 60° C.

The Fischer-indole synthesis to cyclize (V) to (VI) is, of course, effected according to standard procedures such as by heating the reactants in an acidic medium at elevated temperatures, preferably by heating the reactants in acetic acid or in ethanolic hydrochloric acid at reflux temperatures.

The transformation of the 1,2,3,4-tetrahydro-1,3-alkano-5-phenylpyrido [4,3-b] Indole (VI) to the desired 1,2,3,4,4a,9b-hexahydro analog may be effected by a chemical reduction such as, for example treatment of (VI) with an alkali metal (preferably sodium) in liquid ammonia in a solvent such as tetrahydrofuran, diglime or ether.

In those instances where R represents hydrogen and it is desired to obtain final compounds wherein R is lower alkyl, then standard N-alkylation procedures may be employed. Preferably, compounds of formula I wherein R is hydrogen are treated with an acyl halide (e.g., ethyl chloroformate) to form an amide which amide is reduced, preferably with lithium aluminum hydride.

Alternatively, compounds of formula I wherein R is lower alkyl, may be obtained by treatment of those compounds wherein R is hydrogen with alkyl halides in the presence of an alkali metal carbonate or bicarbonate or a lower alkyl tertiary amine in a suitable solvent such as DMF or a lower alkanol.

As stated above, the compounds of formula I may exist as either the d- or l-isomers. The obtention of either the d- or l-forms may be effected by transforming a racemic mixture of either the final product or of the intermediates thereof (e.g., VI or I) into a mixture of two diasteromeric acid addition salts by reaction with suitable optically active acids (e.g., d- or l-dibenzoyl tartaric acid) to produce two diastereomeric salts which are no longer identical (or mirror images) and thus may be separated by conventional physical procedures such as crystallization.

Having described the general routes by which the compounds of this invention (I) may be prepared the following examples will serve to further illustrate the preparation and isolation of these compounds without being limited thereto.

PREPARATION OF HYDRAZONO INTERMEDIATES

EXAMPLE I 5-(2,2-Diphenylhydrazono)-1,3-ethanopiperidine-2-carboxylic acid 2,2,2-trichloroethyl ester 1,1-Diphenylhydrazine hydrochloride (43.5 g) N-2,2,2-trichloroethoxycarbonyl) tropinone (60.6 g) and 30 ml of dry pyridine are stirred together at 60° C. for 1 hour. The mixture is cooled and about 100 ml of isopropanol is added. The solids are filtered, washed with about 100 ml of isopropanol, and air dried to give the desired product.

By replacing the diphenylhydrazine hydrochloride reactant with equivalent quantities of the following reactants
1,1-bis-(p-toluyl)hydrazine hydrochloride,
1,1-bis-(p-methoxyphenyl)hydrazine hydrochloride,
1,1-bis-(p-ethylphenyl)hydrazine hydrochloride,
1-(p-methoxyphenyl)-1-phenylhydrazine hydrochloride, and by substantially following the foregoing procedure, there is produced:
5-2,2-bis-(p-toluyl)hydrazono-1,3-ethanopiperidine-2-carboxylic acid-2,2,2-trichloroethylester,
5-2,2-bis-(4-methoxyphenyl)hydrazono-1,3-ethanopiperidine-2-carboxylic acid-2,2,2-trichloroethylester,
5-2,2-bis-(4-ethylphenyl)hydrazono-1,3-ethanopiperidine-2-carboxylic acid-2,2,2-trichloroethylester,
5-[2-(4-methoxyphenyl)-2-phenyl]hydrazono-1,3-ethanopiperidine-2-carboxylic acid-2,2,2-trichloroethylester.

Similarly, by substituting the N-(2,2,2-trichloroethoxycarbonyl)tropinone with equivalent quantities of N-(2,2,2-trichloroethoxycarbonyl)granitinone and by substantially following the foregoing procedure with the appropriate hydrazines, there are produced
5-(2,2-diphenylhydrazono)-1,3-propanopiperidine-2-carboxylic acid 2,2,2-trichloroethylester,
5-2,2-bis-(p-toluyl)hydrazono-1,3-propanopiperidine-2-carboxylic acid-2,2,2-trichloroethylester,
5-2,2-bis-(4-methoxyphenyl)hydrazono-1,3-propanopiperidine-2-carboxylic acid-2,2,2-trichloroethylester,
5-2,2-bis-(4-ethylphenyl)hydrazono-1,3-propanopiperidine-2-carboxylic acid-2,2,2-trichloroethylester,
5-[2-(4-methoxyphenyl)-2-phenyl]hydrazono-1,3-propanopiperidine-2-carboxylic acid-2,2,2-trichloroethylester.

DEPROTECTION PROCEDURE

EXAMPLE II 5-(2,2-Diphenylhydrazono)-1,3-ethanopiperidine

Zinc dust (90.0 g) is added in small portions to a well-stirred mixture of 5-(2,2-diphenylhydrazono)-1,3-ethanopiperidine-2-carboxylic acid-2,2,2-trichloroethylester in 300 ml of glacial acetic acid, maintaining the reaction temperature between 40° C.–60° C. with external cooling when necessary. Upon completion of the addition, stirring is continued at ambient temperature for 45 minutes. The insoluble material is filtered and the resulting clear yellow filtrate contains the desired product and can be used in the succeeding Fisher-Indole synthesis procedures.

Similarly, the other N-protected intermediates can be subjected to the same procedure to produce a filtrate containing a product ready for the Fisher-Indole synthesis.

FISHER-INDOLE SYNTHESIS

EXAMPLE III 1,2,3,4-Tetrahydro-1,3-ethano-5-phenylpyrido [4,3-b]indole hydrochloride To the clear yellow filtrate obtained in Example II is added 125 ml of isopropanol saturated with dry hydrochloric acid, followed by 125 ml of isopropanol. The resulting mixture is heated at reflux for 2 hours. Upon cooling to room temperature, the precipitated solids are filtered, washed successively with 400 ml of acetone, 400 ml of water and then 400 ml of acetone. The desired product is dried and ready for the next step in the synthesis.

EXAMPLE IV 1,2,3,4-Tetrahydro-1,3-ethano-8-methoxy-5-phenylpyrido [4,3-b]indole hydrochloride A solution of 5-[2-(p-methoxyphenyl)-2-phenylhydrazo]-1,3-ethano-piperidine-2-carboxylic acid, 2,2,2-dichloroethylester (37.0 g), 150 ml of anhydrous ethanol, and 15 ml of phosphoric acid is heated at reflux for 16 hours. At the end of this time, the solvent is evaporated in vacuo, the residue partitioned between water and ether, and the ether solution is evaporated to give an oil. This oil is taken up in 60 ml of glacial acetic acid, and 30.0 g of zinc dust is added in small portions to the stirred solution maintaining a reaction temperature of 50° C.–60° C.

Stirring is continued at ambient temperature for 1 hour after completion of the addition, and the reaction mixture is then filtered. Water is added to the filtrate, and the mixture extracted with ether. The aqueous phase is adjusted to pH 8 with 10% NaOH and extracted with dichloromethane. Ethereal HCl is added to this solution and the precipitated salt is filtered and washed with acetone to yield the desired product.

EXAMPLE V 1,2,3,4-Tetrahydro-1,3-ethano-2-methyl-5-phenyl pyrido [4,3-b]indole hydrochloride 5-(2,2-diphenylhydrazono)-1,3-ethano-2-methyl-piperidine (75 g), prepared from diphenylhydrazine and tropinone is dissolved in 500 ml ethanol, and 300 ml of acetone saturated with HCl added. The mixture is heated at reflux for 1½ hours, and then evaporated to dryness. The residue is taken up in water and extracted with ether. The aqueous layer is basified and extracted with methylene chloride. The extracts are evaporated to give a black gum which is chromatographed on silica gel. The initial eluates are taken with chloroform, then 10:1 chloroform-methanol is used. Fractions shown to be homogeneous by thin layer chromatography are combined and solvent removed. The residue is taken up in ether, some insolubles filtered, and ethereal HCl added to the filtrate. Solids precipitated which are filtered and digested with boiling acetone to give the desired crystalline product.

N-ALKYLATION PROCEDURE

EXAMPLE VI 1,2,3,4-Tetrahydro-1,3-ethano-2-methyl-5-phenyl-pyrido [4,3-b]indole hydrochloride Ethyl chloroformate (1.19 g) in 10 ml of methylenechloride is added (dropwise) to a solution of 1,2,3,4-tetrahydro-1,3-ethano-5-phenylpyrido [4,3-b]indole base (2.7 g) in 40 ml of methylene chloride. On completion of the addition the mixture is heated 1 hour at reflux, cooled and washed successively with water, 5% HCl, and sodium carbonate solution. After drying over anhydrous potassium carbonate, evaporation gives a dark oil. This oil is taken up in 28 ml of dry ether and added to a suspension of 750 mg of lithium aluminum hydride in 50 ml ether. The stirred mixture is heated for 2 hours at reflux, cooled and cautiously decomposed with 10% NaOH solution. The inorganic salts are filtered and the filtrated dried over potassium carbonate. Evaporation of solvent gives a pale yellow oil which, on treatment with ethereal HCl, gives the desired product.

RESOLUTION PROCEDURE

EXAMPLE VII

Resolution of 1,2,3,4-tetrahydro-1,3-ethano-5-phenylpyrido [4,3-b]indole

A solution of the oily free (±) base (21.0 g) in 300 ml methanol is treated with 28.1 g of (−)-dibenzoyltartaric acid. On cooling 23.3 g of salt is obtained. This material is treated with 200 ml boiling methanol and cooled to give 17.8 g of solids. Treatment of the solids with NH$_4$OH and extraction into ether results in an oil product which is treated with ethanolic HCl, the solvent removed in vacuo to give a gummy solid. Treatment of this material with 50 ml of dry acetone gives a crystalline product which is filtered and dried to give white needles, $[\alpha]_D^{26} - 14.2°$ (C=0.5, MeOH).

The mother liquor from the first crystallization above is evaporated in vacuo to give a gum which is then treated with 10% NH$_4$OH. The resulting oily base is extracted with ether, the ether solution washed, dried over anhydrous potassium carbonate and evaporated to an oil.

This oil is dissolved in 200 ml of methanol and treated with 15.0 g (+)-dibenzoyltartaric acid. A solid forms which is filtered giving a salt, $[\alpha]_D^{26} + 78.1°$ (C=0.5 MeOH). The salt is treated with NH$_4$OH, and the oily base extracted into ether. The ethereal solution is washed with water and dried over K$_2$CO$_3$. Evaporation gives an oil which is treated with HCl as the first enantiomer and washed up to give solids $[\alpha]_D^{26} + 12.2°$ (C=0.55, MeOH).

REDUCTION TO FINAL COMPOUNDS

EXAMPLE VIII (1SR,3SR,4aRS,9bSR)-1,2,3,4,4a,9b-hexahydro-1,3-ethano-5-phenylpyrido [4,3-b]indole hydrochloride (±) 1,2,3,4-tetrahydro-1,3-ethano-5-phenylpyrido [4,3-b]indole hydrochloride (13.0 g) is converted to the oily free base by stirring with 10% NH$_4$OH solution and extraction of the resulting produce into ether. The ethereal solution is washed with water, dried over anhydrous potassium carbonate and solvent is evaporated.

The base is dissolved in 70 ml of dry tetrahydrofuran and added to about 150 ml of anhydrous liquid ammonia. Sodium metal (3.0 g) is added to the stirred yellow solution until a deep blue-black color persists. The resulting mixture is stirred for 30 minutes, and then sufficient solid ammonium chloride is added to discharge the blue color. The ammonia is then distilled from the mixture while replacing it with ether. Upon removal of all of the ammonia, the mixture is treated with sufficient water, separated, dried over anhydrous potassium carbonate, and evaporated in vacuo to give an oil which quickly solidifies and on recrystallization from hexane gives 7.1 g of product, m.p. 109°–110°.

In a similar manner, the (+) enantiomer described above gives a product $[\alpha]_D^{26} -146.8°$ (C=1.2, MeOH) m.p. 116.7°, and the (−) enantiomer gives a product $[\alpha]_D^{26} +148.1°$ (C=2.1 MeOH), m.p. 116.5°–117.5°.

Similarly, by use of the appropriate starting materials and by substantially following the procedures of the foregoing examples, there is produced the following 1,2,3,4,4a,9b-hexahydro-1,3-alkano-2-R-5-phenylpyrido[4,3-b]indoles.

| X | Y | Q | R |
|---|---|---|---|
| 8-OCH₃ | 4-OCH₃ | ethano | H |
| H | H | propano | H |
| 8-OCH₃ | H | ethano | H |
| 8-CH₃ | 4-CH₃ | ethano | CH₃ |
| 8-CH₃ | 4-CH₃ | ethano | H |

As stated above, the compounds of this invention (I) are anti-depressants useful in the treatment of mental depression of either endogenous or acute (ie, reactive) nature.

The anti-depressant activity of the compounds of this invention may be ascertained by testing in standard biological test procedures (eg, the rat muricide test, and tetrabenazine induced stereotypy in rats). The testing is effected both in terms of their absolute activity and also by comparison against such well-known standards as the amitryptyline and imipramine. On the basis of the standard testing procedures, either above or on a comparative basis, it is found that these compounds (I) exert their anti-depressant activity in the treatment of mental depression at dosage levels of about 1 to 10 MPK per day, preferably in 3–4 divided doses. In addition to the results of the foregoing test procedures, it is also found that the compounds of this invention will have, when compared to such compounds as imipramine or amitryptyline, a relatively fast onset of action and will exert little or not anticholinergic side effects.

In their use as anti-depressants the compounds may be prepared into standard pharmaceutical formulations suitable for oral, rectal, or parenteral administration by formulation techniques well known in the art, such as for example tablets, capsules, aqueous or oily suspensions or solutions, emulsions, powders, suppositories and the like. Suitable adjuvants such as calcium carbonate, starch, lactose, talc, magnesium stearate, gum acacia and the like are advantageously used.

Preferred compounds of this invention are those wherein Q is ethano, X is hydrogen or methoxy (preferably in the 8-position) Y is hydrogen and R is hydrogen or methyl.

In those instances wherein the desired compound has a hydroxy group as the X and/or Y substituent, these compounds may be prepared by de-alkylation of the corresponding alkoxy compound using a strong protonic acid or a Lewis acid.

We claim:
1. A compound of the formula

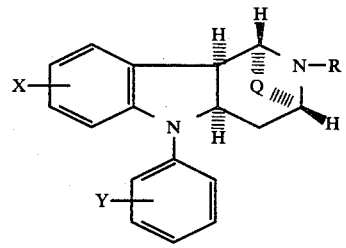

and to their pharmaceutically acceptable alkali metal, lower alkyl and benzyl quaternary and acid addition salts wherein R is hydrogen or lower alkyl, X and Y each are hydrogen, hydroxy, lower alkoxy and lower alkyl, and Q is (CH₂)n wherein n is 2 or 3.

2. A compound of claim 1 wherein R is hydrogen.

3. A compound of claim 1 wherein Q is ethano.

4. A compound of claim 3 wherein R, X and Y are hydrogen.

5. A compound of claim 3 wherein R and Y are hydrogen and X is a 8-methoxy.

6. A compound of claim 3 wherein R is hydrogen, Y is P-CH₃ and X is 8-CH₃.

* * * * *